(12) United States Patent
Kondoh et al.

(10) Patent No.: US 7,720,527 B2
(45) Date of Patent: May 18, 2010

(54) SUBCUTANEOUS FAT THICKNESS MEASURING METHOD, SUBCUTANEOUS FAT THICKNESS MEASURING APPARATUS, PROGRAM AND RECORDING MEDIUM

(75) Inventors: Kazuya Kondoh, Osaka (JP); Shinji Uchida, Osaka (JP)

(73) Assignee: Panasonic Corp., Osaka (JP)

( * ) Notice: Subject to any disclaimer, the term of this patent is extended or adjusted under 35 U.S.C. 154(b) by 483 days.

(21) Appl. No.: 10/986,719

(22) Filed: Nov. 12, 2004

(65) Prior Publication Data

US 2005/0107707 A1     May 19, 2005

(30) Foreign Application Priority Data

Nov. 14, 2003   (JP)   ............... 2003-385493

(51) Int. Cl.
*A61B 6/00* (2006.01)
(52) U.S. Cl. .................................... 600/476
(58) Field of Classification Search ................ 600/500, 600/438, 475, 473, 476
See application file for complete search history.

(56) References Cited

U.S. PATENT DOCUMENTS

| | | | | |
|---|---|---|---|---|
| 5,014,713 | A * | 5/1991 | Roper et al. | 600/473 |
| 6,587,702 | B1 * | 7/2003 | Ruchti et al. | 600/310 |
| 6,622,095 | B2 * | 9/2003 | Kobayashi et al. | 702/31 |
| 2002/0173780 | A1 | 11/2002 | Altshuler et al. | |
| 2004/0039287 | A1 * | 2/2004 | Horiuchi et al. | 600/476 |

FOREIGN PATENT DOCUMENTS

| | | |
|---|---|---|
| EP | 0 516 251 | 12/1992 |
| EP | 0 942 260 | 9/1999 |
| EP | 1 013 219 A1 | 6/2000 |
| JP | 11-239573 | 9/1999 |
| JP | 2000-155091 | 6/2000 |
| JP | 2003-265440 A | 9/2003 |
| WO | WO98/23916 | 6/1998 |
| WO | WO 03/063704 A1 | 8/2003 |

OTHER PUBLICATIONS

European Search Report for EP 04 02 7102, dated Jan. 20, 2005.

* cited by examiner

*Primary Examiner*—Brian Casler
*Assistant Examiner*—Elmer Chao
(74) *Attorney, Agent, or Firm*—RatnerPrestia

(57) ABSTRACT

A subcutaneous fat thickness measuring apparatus includes: a light source section that irradiates a surface of a living body with plural light rays having different central wavelengths; a light receiving section that receives the plural light rays of different wavelengths emerging from the surface of a living body and determining the quantities of the plural light rays received; and a calculator section that calculates the thickness of subcutaneous fat of the surface of a living body from the quantities of the plural light rays received measured by the light receiving section using a previously determined relationship among subcutaneous fat thicknesses, blood concentrations in subcutaneous fat and quantities of plural light rays having different central wavelengths.

17 Claims, 12 Drawing Sheets

SUBCUTANEOUS FAT THICKNESS MEASURING METHOD, SUBCUTANEOUS FAT THICKNESS MEASURING APPARATUS, PROGRAM AND RECORDING MEDIUM

BACKGROUND OF THE INVENTION

1. Field of the Invention

The present invention relates to a subcutaneous fat thickness measuring method of optically measuring the thickness of local subcutaneous fat, a subcutaneous fat thickness measuring apparatus, a program and a recording medium.

2. Related Art of the Invention

As shown in FIG. 13, there is a conventional method of measuring the thickness of subcutaneous fat 4 in a living body by a light receiving element 3 receiving light that is launched into the living body by a light source 2 on a surface of a living body 1, passes through the living body while being scattered and absorbed therein, and then emerges from the surface of a living body (for example, see Japanese Patent Laid-Open No. 2000-155091). The entire disclosure of the above document is incorporated herein by reference in its entirety. In addition, in the above document, there is disclosed a method of compensating for a variation due to a difference of the color of a skin 5 using the quantity of light received by a light receiving element 3 disposed near the light source.

The muscle and the fat have significantly different light propagation characteristics. The muscle absorbs more light, and the fat scatters more light. The difference in light propagation characteristics is remarkable for light having a wavelength between 500 nm and 1000 nm. Therefore, as the subcutaneous fat 4 becomes thicker, more light launched by the light source 2 into the surface of a living body is scattered in the subcutaneous fat 4 and is diffused not only in the depth direction but also in the lateral direction.

Thus, the light diffused in the lateral direction and emerges from the surface of a living body 1 increases according to increment of the thickness of the subcutaneous fat 4. The thickness and the amount of the subcutaneous fat 4 can be determined by the light receiving element 3 receiving the light emerging from the surface of a living body 1.

In addition, according to this method, the light source 2 and plural light receiving elements 3 are disposed so that plural light-reception-to-light-emission lengths can be obtained. That is, in determining the quantity of light received by each light receiving element 3, an error due to a difference of the color of the skin 5 is compensated for using the quantity of light received by the light receiving element disposed closest to the light source 2.

However, although the conventional subcutaneous fat thickness measuring apparatus described above can correct an error due to a difference of the color of the skin 5, it cannot correct an error due to a variation of light absorption by the subcutaneous fat 4, which is caused by a variation of the blood amount.

The subcutaneous fat 4 of a human body, which is a measuring object, has a network of blood vessels and can effectively be regarded as a uniform organization. However, the amount of the blood flowing through the organization varies due to exercise or sleep, which causes the blood concentration to vary, which causes the light absorption by the subcutaneous fat 4 to vary.

As described above, the conventional subcutaneous fat thickness measuring apparatus has a problem that it cannot correct an error due to a variation of light absorption by the subcutaneous fat 4.

SUMMARY OF THE INVENTION

To solve the problem described above, an object of the present invention is to provide a subcutaneous fat thickness measuring method that can obtain information about subcutaneous fat, such as the thickness of subcutaneous fat, with high precision and reproducibility, a subcutaneous fat thickness measuring method, a program and a recording medium.

The $1^{st}$ aspect of the present invention is a subcutaneous fat thickness measuring method, comprising:

an irradiation step of irradiating a surface of a living body with plural light rays having different central wavelengths;

a light receiving step of receiving said plural light rays of different wavelengths emerging from said surface of a living body and measuring the quantity of each of the plural light ray received; and a calculation step of calculating the thickness of subcutaneous fat of said living body from said quantities of the plural light rays received measured in said light receiving step using a relationship between subcutaneous fat thicknesses and quantities of plural light rays having different central wavelengths, in case that blood concentrations in the subcutaneous fat are different each other.

The $2^{nd}$ aspect of the present invention is the subcutaneous fat thickness measuring method according to the $1^{st}$ aspect of the present invention, wherein said relationship is a relationship between the quantity of each of said plural light rays received which is obtained in steps corresponding to said irradiation step and said light receiving step performed for a surface of a living body having a known subcutaneous fat thickness and said known subcutaneous fat thickness, and there are plural relationships between the quantity of light received and the subcutaneous fat thickness for plural blood concentrations.

The $3^{rd}$ aspect of the present invention is the subcutaneous fat thickness measuring method according to the $2^{nd}$ aspect of the present invention, wherein said calculation step includes:

comparing the known subcutaneous fat thicknesses respectively corresponding to the quantities of the plural light rays received obtained in said light receiving step for the blood concentrations; and finding such relationship between the blood concentration and the known subcutaneous fat thickness that the same value in common with the quantities of the plural light rays received is obtained and determining the known subcutaneous fat thickness given by the found relationship as the subcutaneous fat thickness of said surface of a living body.

The $4^{th}$ aspect of the present invention is the subcutaneous fat thickness measuring method according to the $1^{st}$ aspect of the present invention, wherein said plural light rays are two light rays of a first central wavelength and a second central wavelength, said first central wavelength falls between 650 nm and 700 nm, and said second central wavelength falls between 800 nm and 850 nm.

The $5^{th}$ aspect of the present invention is the subcutaneous fat thickness measuring method according to the $1^{st}$ aspect of the present invention, wherein, in said light receiving step, said plural light rays of different wavelengths emerging from said surface of a living body are received at a plurality of sites on said surface of a living body.

The $6^{th}$ aspect of the present invention is the subcutaneous fat thickness measuring method according to the $1^{st}$ aspect of the present invention, further comprising:

a body fat percentage calculation step of calculating the body fat percentage of a measuring object person from the calculated thickness of subcutaneous fat by using information about all or some of the weight, the sex, the height, the age and the measurement part of the measuring object person having said surface of a living body.

The 7$^{th}$ aspect of the present invention is a subcutaneous fat thickness measuring apparatus, comprising:

irradiation means of irradiating a surface of a living body with plural light rays having different central wavelengths;

light receiving means of receiving said plural light rays of different wavelengths emerging from said surface of a living body and measuring the quantity of each of the plural light ray received; and calculation means of calculating the thickness of subcutaneous fat of said living body from said quantities of the plural light rays received measured by said light receiving means using a relationship between subcutaneous fat thicknesses and quantities of plural light rays having different central wavelengths, in case that blood concentrations in the subcutaneous fat are different each other.

The 8$^{th}$ aspect of the present invention is the subcutaneous fat thickness measuring apparatus according to the 7$^{th}$ aspect of the present invention, wherein said relationship is a relationship between the quantity of each of said plural light rays received which is obtained by said irradiation means and said light receiving means performing the respective operations for a surface of a living body having a known subcutaneous fat thickness under the same conditions and said known subcutaneous fat thickness, and there are plural relationships between the quantity of light received and the subcutaneous fat thickness for plural blood concentrations.

The 9$^{th}$ aspect of the present invention is the subcutaneous fat thickness measuring apparatus according to the 8$^{th}$ aspect of the present invention, wherein said calculation means:

compares the known subcutaneous fat thicknesses respectively corresponding to the quantities of the plural light rays received obtained by said light receiving means for the blood concentrations; and finds such relationship between the blood concentration and the known subcutaneous fat thickness that the same value in common with the quantities of the plural light rays received is obtained and determines the known subcutaneous fat thickness given by the found relationship as the subcutaneous fat thickness of said surface of a living body.

The 10$^{th}$ aspect of the present invention is the subcutaneous fat thickness measuring apparatus according to the 7$^{th}$ aspect of the present invention, wherein said plural light rays emitted by said irradiation means are two light rays of a first central wavelength and a second central wavelength, said first central wavelength falls between 650 nm and 700 nm, and said second central wavelength falls between 800 nm and 850 nm.

The 11$^{th}$ aspect of the present invention is the subcutaneous fat thickness measuring apparatus according to the 7$^{th}$ aspect of the present invention, wherein said light receiving means receives said plural light rays of different wavelengths emerging from said surface of a living body at a plurality of sites on said surface of a living body.

The 12$^{th}$ aspect of the present invention is the subcutaneous fat thickness measuring apparatus according to the 7$^{th}$ aspect of the present invention, further comprising:

body fat percentage calculation means of calculating the body fat percentage of a measuring object person from the calculated thickness of subcutaneous fat by using information about all or some of the weight, the sex, the height, the age and the measurement part of the measuring object person having said surface of a living body.

The 13$^{th}$ aspect of the present invention is a program that makes a computer execute a calculation step of a subcutaneous fat thickness measuring method according to the 1$^{st}$ aspect of the present invention, said calculation step being to calculate the thickness of subcutaneous fat of a living body from said quantities of plural light rays received measured in said light receiving step using a relationship between subcutaneous fat thicknesses and quantities of plural light rays having different central wavelengths, in case that blood concentrations in the subcutaneous fat are different each other.

The 14$^{th}$ aspect of the present invention is a recording medium that can be processed by a computer and stores a program according to the 13$^{th}$ aspect of the present invention.

According to the present invention, there are provided a subcutaneous fat thickness measuring method that can obtain information about subcutaneous fat, such as the thickness of subcutaneous fat, with high precision and reproducibility, a subcutaneous fat thickness measuring method, a program and a recording medium.

DESCRIPTION OF SYMBOLS

Figure 1:
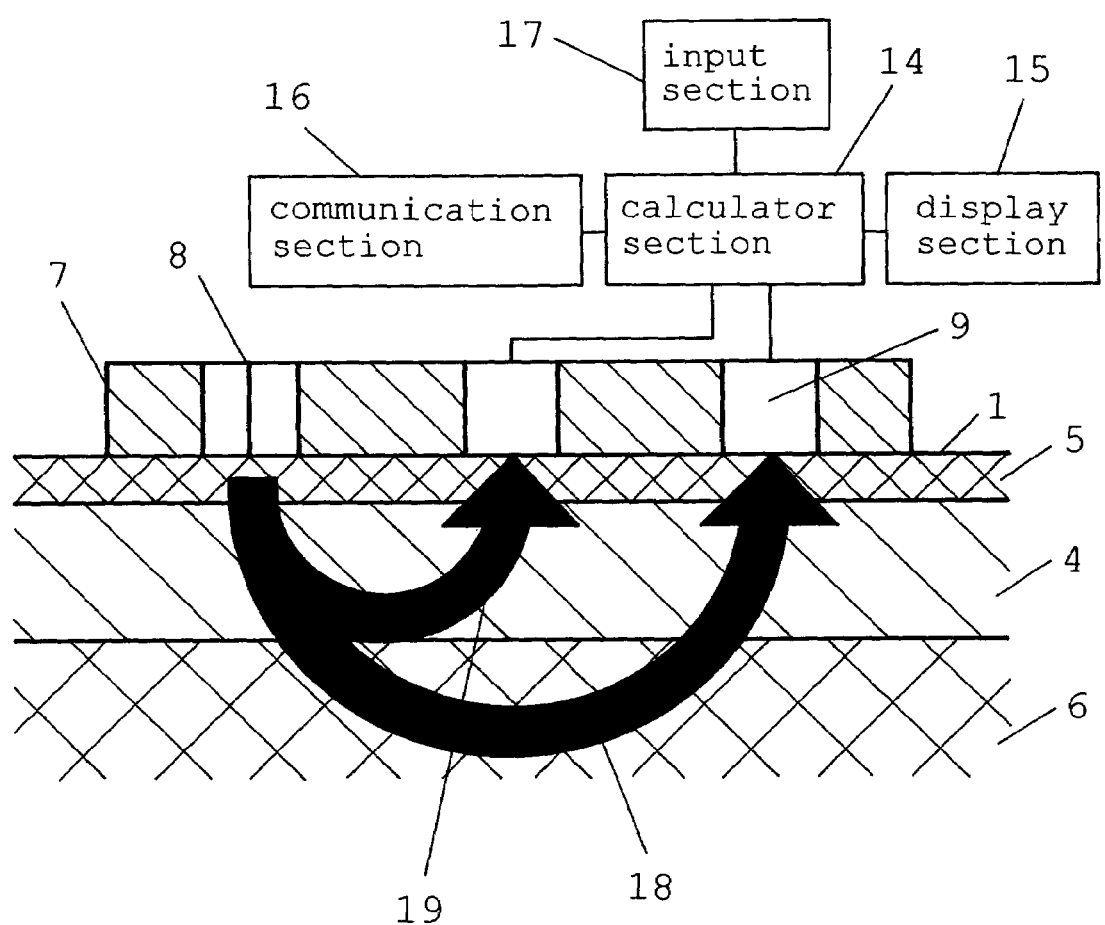
FIG. 1 is a diagram showing an optical subcutaneous fat thickness measuring apparatus according to an embodiment of the present invention.

1 Surface of a living body
2 Light source
3 Light receiving element
4 Fat
5 Skin
6 Muscle
7 Shaping section
8 Light source section
9 Light receiving section
10 Measuring light receiving element
11 Compensating light receiving section
12 First light source
13 Second light source
14 Calculator section
15 Display section
16 Communication section
17 Input section
18 Light reaching measuring light receiving element
19 Light reaching compensating light receiving element

PREFERRED EMBODIMENTS OF THE INVENTION

In the following, embodiments of the present invention will be described with reference to the drawings.

First Embodiment

First, a first embodiment will be described.

Figure 2:
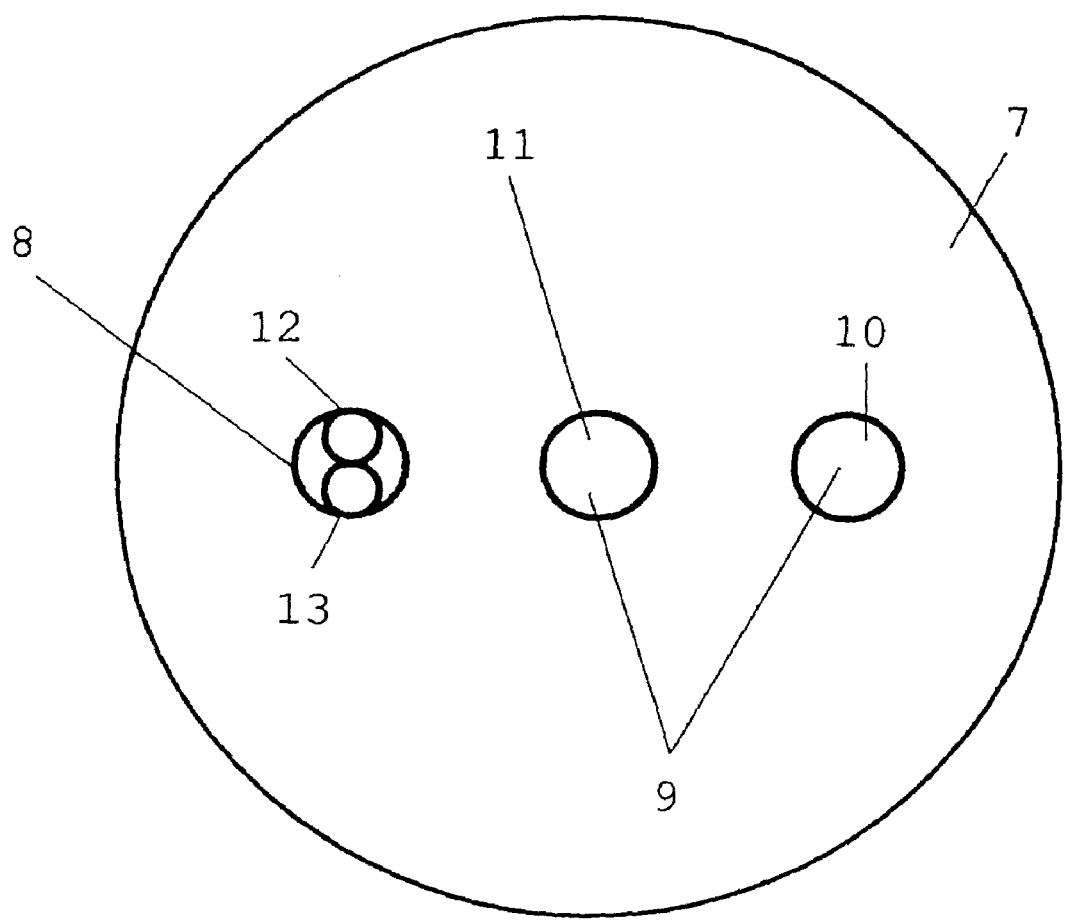
FIG. 2 is a top view of a shaping section of the optical subcutaneous fat thickness measuring apparatus, viewed from the side of a surface of a living body.

FIG. 1 is a block diagram showing a subcutaneous fat measuring apparatus according to this embodiment, and FIG. 2 is a top view of a shaping section 7 of the subcutaneous fat measuring apparatus, viewed from the side of a surface of a living body 1.

The subcutaneous fat measuring apparatus according to this embodiment is capable of compensating for variations of light absorption by a fat layer 4. Besides blood, the skin 5 and the muscle 6 contain melanin and myoglobin, respectively, which are constituents that absorb a significant quantity of light. However, since the subcutaneous fat 4 does not contain melanin and myoglobin, the blood primarily absorbs light. That is, a variation of light absorption by the subcutaneous fat 4 is primarily caused by variation of the blood amount therein. It is known that the light absorption spectrum of the blood varies with the oxygen concentration. When a living body is in a resting state, the oxygen concentration is steady, and therefore, the light absorption spectrum of the blood in the subcutaneous fat 4 is also steady. Thus, by using, of light rays that can easily pass through the living body, a plurality of light rays of wavelengths from 650 nm, which is more absorbed by the blood, to 850 nm, which is less absorbed by the blood, the variations of light absorption in the subcutaneous fat 4 can be compensated for.

In addition, by calculating the thickness of the subcutaneous fat from the measurements for two central wavelengths in the vicinities of 650 nm and 850 nm, whose light absorptions differ particularly remarkably, the thickness of the subcutaneous fat can be determined more precisely.

In addition, by receiving light from the surface of a living body 1 at plural sites on the surface of a living body 1, a variation of the color of the skin 5 can be compensated for, and thus, the thickness of the subcutaneous fat can be determined more precisely.

In addition, by taking into consideration information about weight, sex, height, age, measurement site or the like, the body fat percentage, which is strongly related with the subcutaneous fat thickness, can be calculated.

Referring to FIGS. 1 and 2, on the surface of a living body 1 composed of three layers or the skin 5, the subcutaneous fat 4 and the muscle 6, the shaping section 7 that substantially flattens the surface of a living body 1 is provided.

In the shaping section 7, a light source section 8 having two light sources and a light receiving section 9 are provided. The light receiving section 9 is composed of a measuring light receiving element 10 (second light receiving element) and a compensating light receiving element 11 (first light receiving element). The distance between the measuring light receiving element 10 and the light source section 8 is 35 mm, and the distance between the compensating light receiving element 11 and the light source section 8 is 20 mm. A light emission opening of the light source section 8 has a diameter of 5 mm, and light entrance openings of the measuring light receiving element 10 and the compensating light receiving element 11 have a diameter of 5 mm. Here, the distance between the measuring light receiving element 10 and the light source section 8 preferably falls within the range from 35 mm to 80 mm, and the distance between the compensating light receiving element 9 and the light source section 6 preferably falls within the range from 15 mm to 30 mm. Here, a first light source 12 of the light source section 8 is an LED having a central wavelength of 660 nm. A second light source 13 which is also provided with the light source section 8 is an LED having a central wavelength of 850 nm.

It is preferable that the first light source 12 and the second light source 13 are light source elements, such as a laser diode or an LED, having a central wavelength of 650 nm to 700 nm and a central wavelength of 800 nm to 850 nm, respectively, because the difference of the respective light absorptions by the blood becomes significant. Furthermore, it is preferable that a light guiding member, such as an optical fiber, is used to guide the light from the light source elements to the surface of a living body 1, because heat generated in the light source elements is not transferred to the surface of a living body 1.

The light receiving elements of the light receiving section 9 used herein are photodiodes. The light receiving elements may be a photoelectric transducer, such as Cds. Furthermore, a light guiding member, such as an optical fiber, may be used to guide the light from the surface of a living body to the light receiving elements.

In addition, the shaping section 7 is substantially flat, so that the surface of a living body 1 is stably made flat, and thus, the reproducibility of measurement is improved. The shaping section 7 has a disk-like shape having a diameter of 60 mm and is made of black ABS for light shielding. Since the material of the shaping section 7 has low reflectivity with respect to light from the light source section 8, return of the light from the surface of a living body 1 into the living body can be prevented, and the light receiving section 9 can receive only the light having propagated through a deep part of the living body. Thus, the measurement precision is improved. In addition, the material can block disturbance light, which will be a noise, from the surroundings of the light source section 8, so that the measurement precision is further improved. The shaping section 7 is chamfered so that no sharp edge comes into contact with the surface of a living body 1, and thus, even if the shaping section is pressed against the surface of a living body, the measuring object person feels no pain due to a sharp edge.

A calculator section 14 calculates the thickness of the subcutaneous fat 4 based on the quantity of light received obtained by the light receiving section 9. The thickness of the subcutaneous fat 4 calculated is displayed on a display section 15, and sent, as data, to another device via a communication section 16.

If data concerning the height, weight, age, sex, measurement portion or the like of the measuring object person is input directly via an input section 17 or input from another device via the communication section 16, the body fat percentage, which is related with the thickness of the subcutaneous fat 4, can also be calculated by the calculator section 14 and displayed on the display section 15 or transferred, as data, to another device via the communication section 16.

Figure 4:
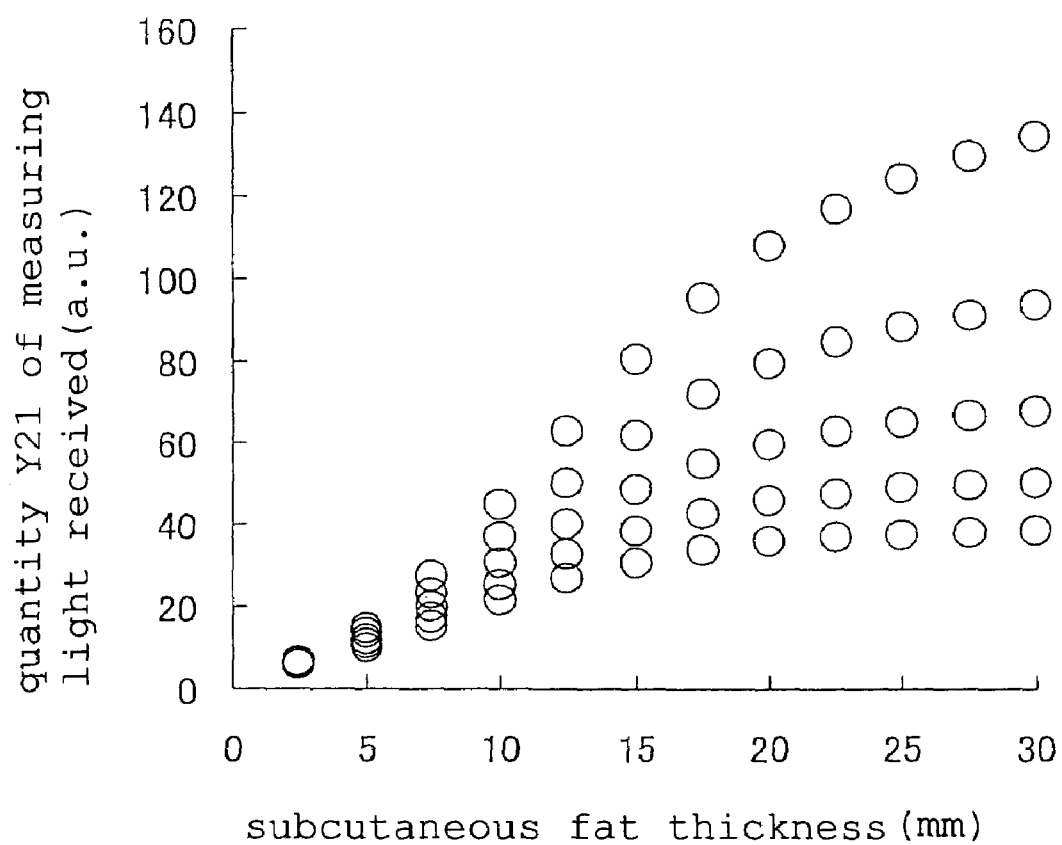
FIG. 4 is a graph showing a relationship between the quantity of measuring light received which, by simulation, takes into account a variation of light absorption by fat and the subcutaneous fat thickness.

Now, a method of correcting a measurement error occurring when the blood concentration in the subcutaneous fat varies will be described. According to the conventional technique, the quantity of the light varies with the blood concentration in the subcutaneous fat 4, and the variation causes a measurement error in the calculator section 14. This can be apparently seen from the fact that, if the blood concentration in the subcutaneous fat 4 varies, the simulation result of the quantity of the light of a wavelength of 800 nm received varies as shown in FIG. 4 by white dots, and it is difficult to determine the fat thickness from the quantity of light.

Thus, of light rays of wavelengths from 600 nm to 850 nm, a light ray of a wavelength between 650 nm to 700 nm, which is more absorbed by the blood, and a light ray of a wavelength between 800 nm and 850 nm, which is less absorbed by the blood, are used, thereby enabling correction of the measurement error due to the variation of the blood concentration in the subcutaneous fat 4.

Figure 8:
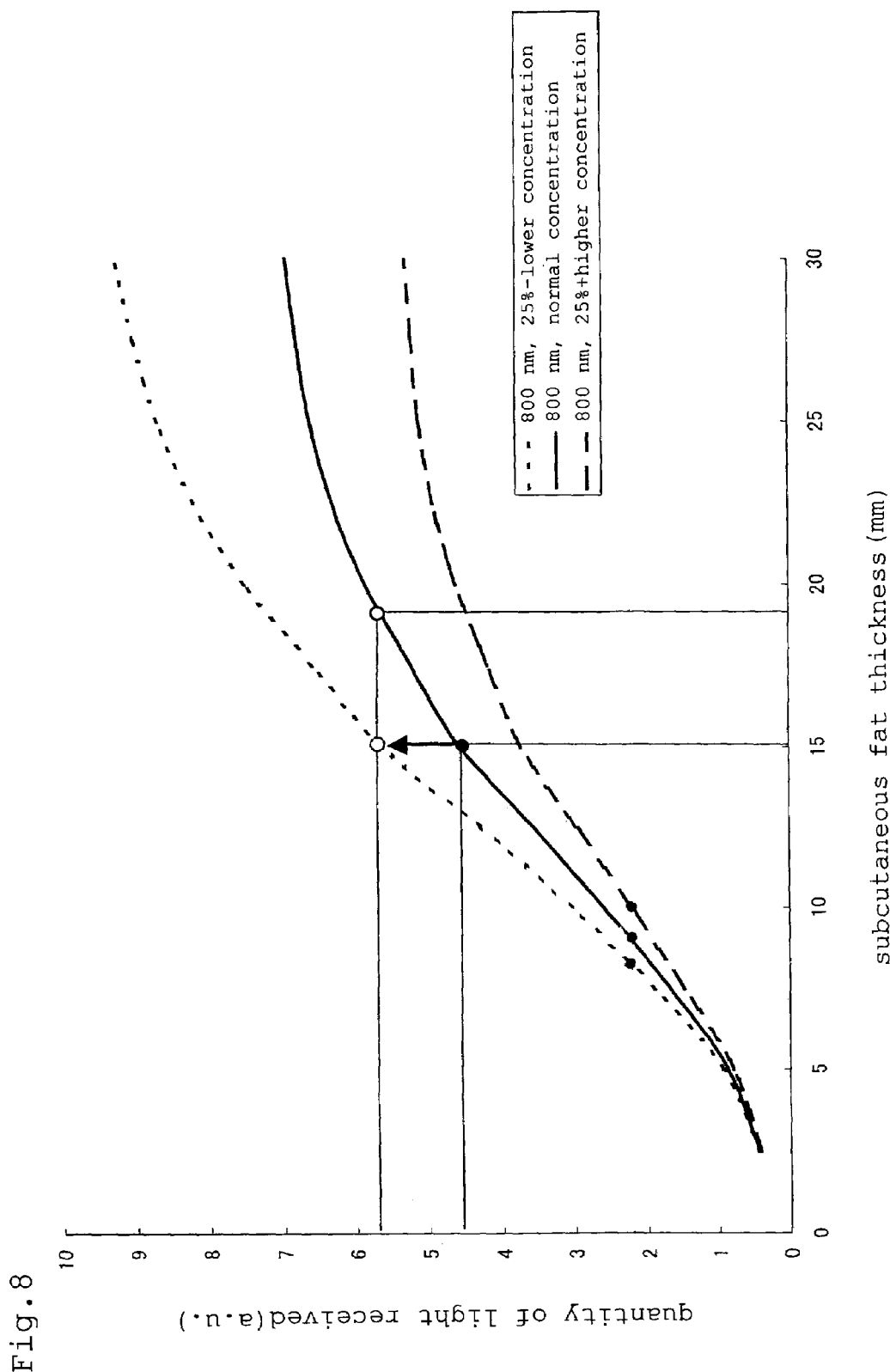
FIG. 8 shows a relationship between the subcutaneous fat thickness and the quantity of light of a wavelength of 800 nm received, which is determined by simulation.
Figure 9:
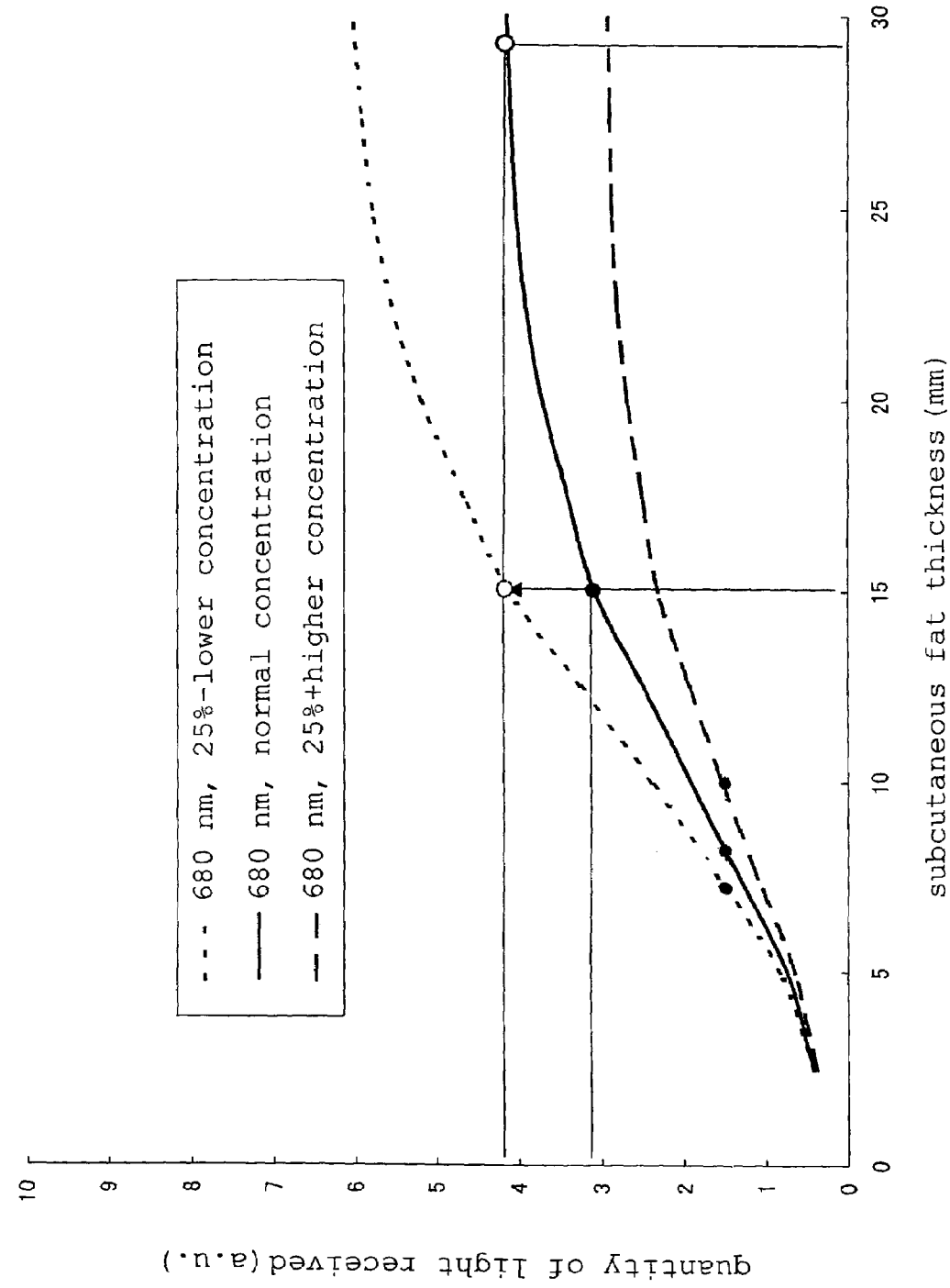
FIG. 9 shows a relationship between the subcutaneous fat thickness and the quantity of light of a wavelength of 680 nm received, which is determined by simulation.

FIG. 8 shows a relationship, determined by simulation, between the quantity of light received and a known subcutaneous fat thickness in the case where a light source having a central wavelength of 800 nm for the cases where the blood concentration in the fat layer is at a normal level, where the blood concentration increases from the normal level by 25% (25%-higher blood concentration) and where the blood concentration decreases from the normal level by 25% (25%-lower blood concentration). FIG. 9 shows a relationship, determined by simulation, between the quantity of light received and a known subcutaneous fat thickness in the case where a light source having a central wavelength of 680 nm for the same conditions of blood concentration as in FIG. 8.

For the known subcutaneous fat thickness of 15 mm as a true value, the quantity of light received is the highest for the 25%-lower blood concentration for the both light rays. If the quantity of light received is applied to the graph for the case of the normal blood concentration, the resulting subcutaneous fat thickness is larger than the true value. However, since the graphs for the two wavelengths vary with respect to the blood concentration differently, the subcutaneous fat thickness is calculated at about 18 mm for the 800-nm light, and the subcutaneous fat thickness is calculated at about 28 mm for the 680-nm light. In this way, the subcutaneous fat thickness is calculated at different values for the two wavelengths.

From the fact that the measurement of the subcutaneous fat thickness using two light rays of different wavelengths result in different values as described above, it can be seen that the variation of the blood concentration causes the variation of the measurement result.

Figure 3:
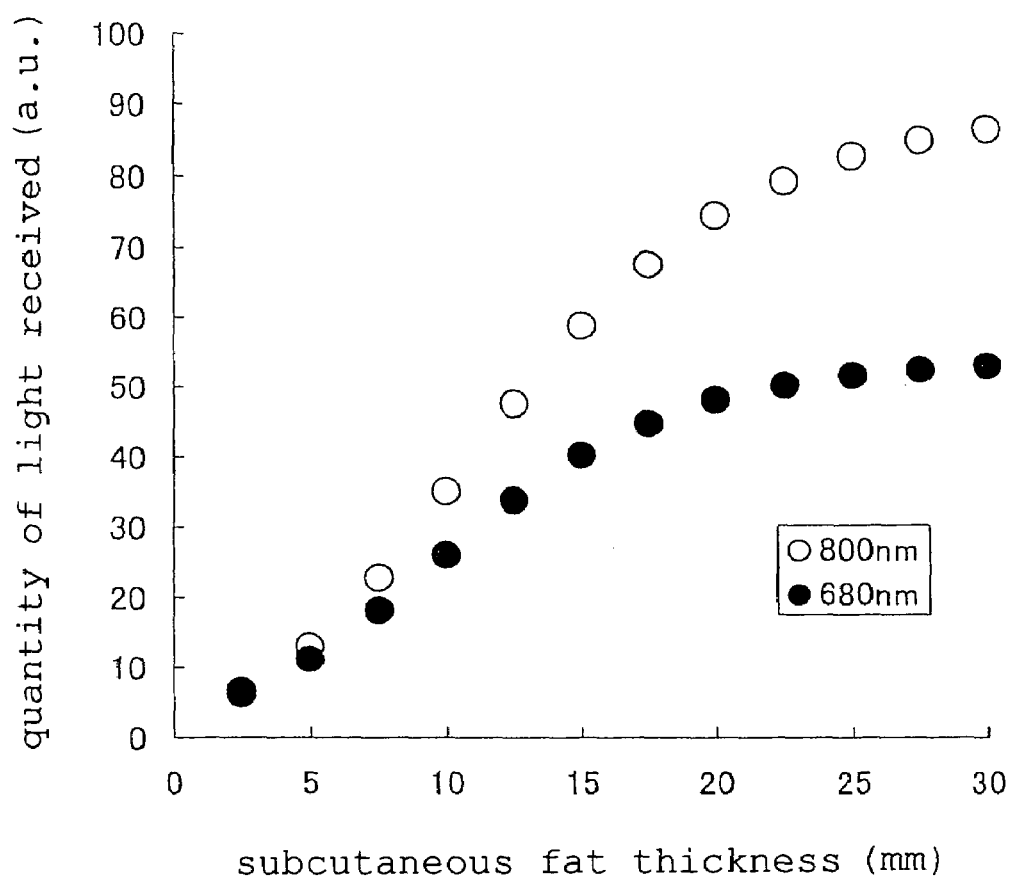
FIG. 3 is a graph showing a relationship between the quantity of measuring light received and the subcutaneous fat thickness, determined by simulation.
Figure 10:
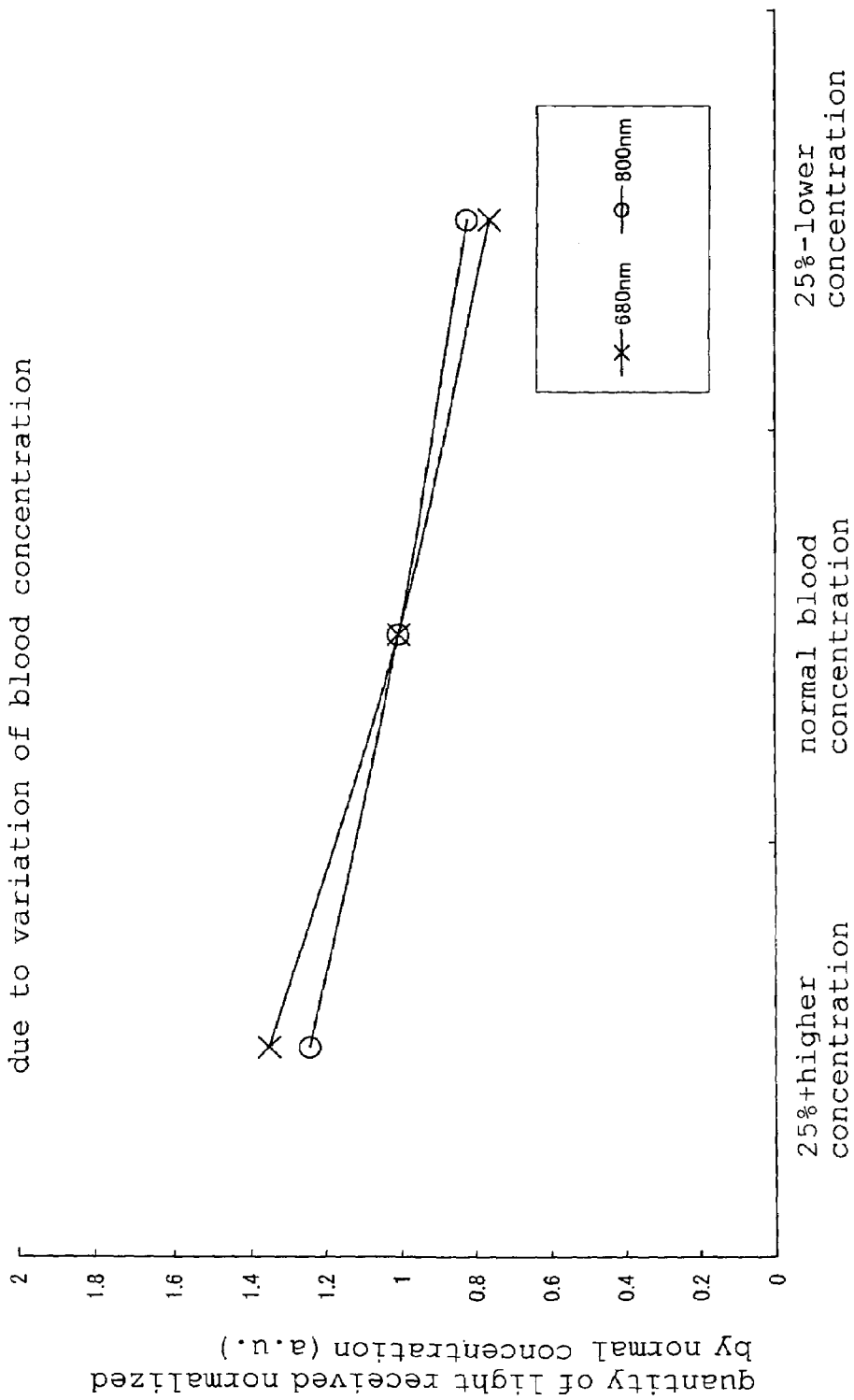
FIG. 10 is a graph for comparing the variations of the quantities of light of a wavelength of 680 nm and light of a wavelength of 800 nm received due to a variation of the blood concentration.

The 800-nm light and the 680-nm light differ from each other in the variation of the quantity of light received due to the variation of the blood concentration and in the variation of the quantity of light received due to the variation of the subcutaneous fat thickness. That is, in addition to the fact described above with reference to FIG. 3 that the quantity of light received increases as the wavelength of the light used for measurement becomes longer, a variation of the blood concentration makes the quantity of light received vary smaller for a light ray having a longer central wavelength if light rays having different central wavelengths are used for measurement, as shown in FIG. 10.

Paying attention to this point, the variation of the blood concentration in the subcutaneous fat 4 can be compensated for by a conversion formula determined by regression analysis using the quantities of the two light rays of different wavelengths as parameters.

Now, a procedure of the measurement using such a conversion formula will be described.

As a first operation, in a state where the light source section 8 is off, the shaping section 7 is pressed against the surface of a living body 1.

As a second operation, the first light source 12 is turned on. Light 18 having reached the measuring light receiving element 10 is measured to obtain the quantity Y21 of measuring light received.

As a third operation, the first light source 12 is turned off, and the second light source 13 is turned on. The light 18 having reached the measuring light receiving element 10 is measured to obtain the quantity Y22 of measuring light received.

As a fourth operation, the thickness of the subcutaneous fat 14 is calculated in the calculator section 14. The thickness X of the subcutaneous fat can be determined by the following formula 1.

[Formula 1]

$$X = A \times Y22 + B \times Y21 + C \quad \text{(formula 1)}$$

Here, characters A, B and C denote constants, which are determined by regression analysis from combinations of the quantities Y21 and Y22 of light received obtained by measurement for plural living bodies whose subcutaneous fat thicknesses X are known in case that blood concentrations in the subcutaneous fat are different each other. The known subcutaneous fat thicknesses X can be determined from images taken by ultrasonic diagnostic equipment, MRI or X-ray CT. If the subcutaneous fat and the quantity Y21 and Y 22 is obtained, the constants A, B and C can be obtained without measuring a blood concentration in the subcutaneous. Therefore the formula 1 reflects a relationship between subcutaneous fat thicknesses and quantities of plural light rays having different central wavelengths, in case that blood concentrations in the subcutaneous fat are different each other.

Figure 5:
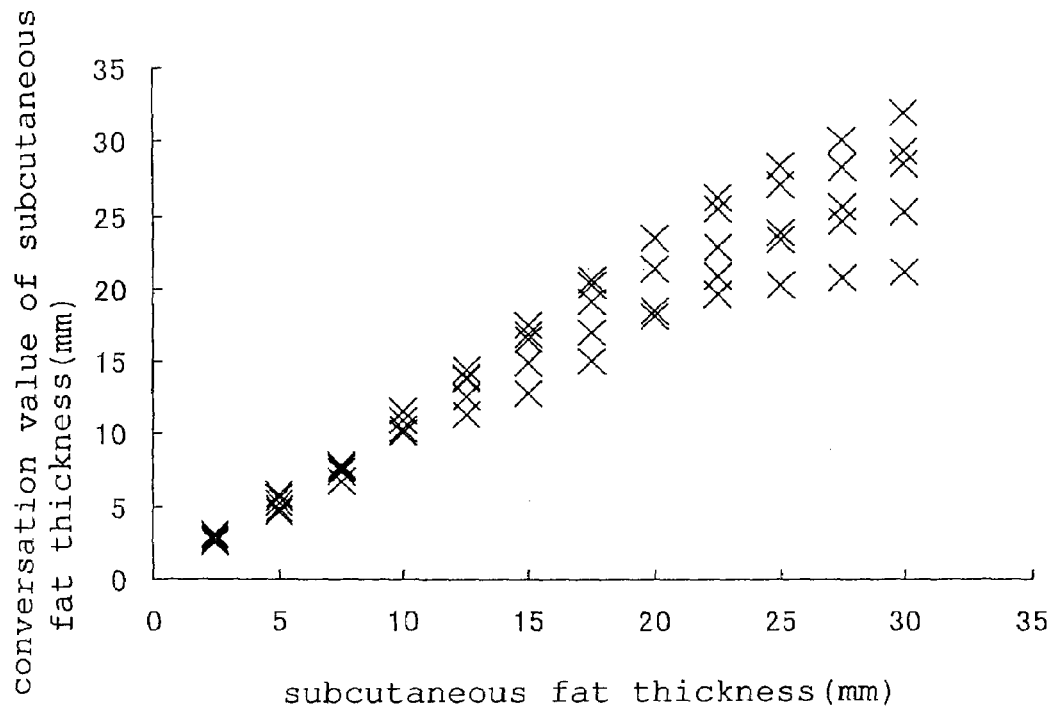
FIG. 5 is a graph showing a relationship between the conversation value of subcutaneous fat thickness value that is determined by a conversion formula and compensated for a variation of light absorption by fat and the subcutaneous fat thickness.

The quantities Y22 and Y21 of the light of the two wavelengths received for the case where the light absorption by the subcutaneous fat 4 varies are calculated, and the parameters A, B and C are determined based on the calculation result. FIG. 5 shows a relationship between values of the subcutaneous fat thickness determined from the formula 1 and the quantities of light received and values of the subcutaneous fat thickness, which are simulation conditions. From comparison of FIGS. 4 and 5, it can be seen that, in FIG. 5, the variation of the subcutaneous fat thickness is suppressed, and the variation of light absorption by the subcutaneous fat is compensated for. It is preferable that the formula 1 of a conversion formula is stored in the calculator section 14 corresponding to the calculating means of the present invention.

Now, another correcting method will be described.

Figure 11:
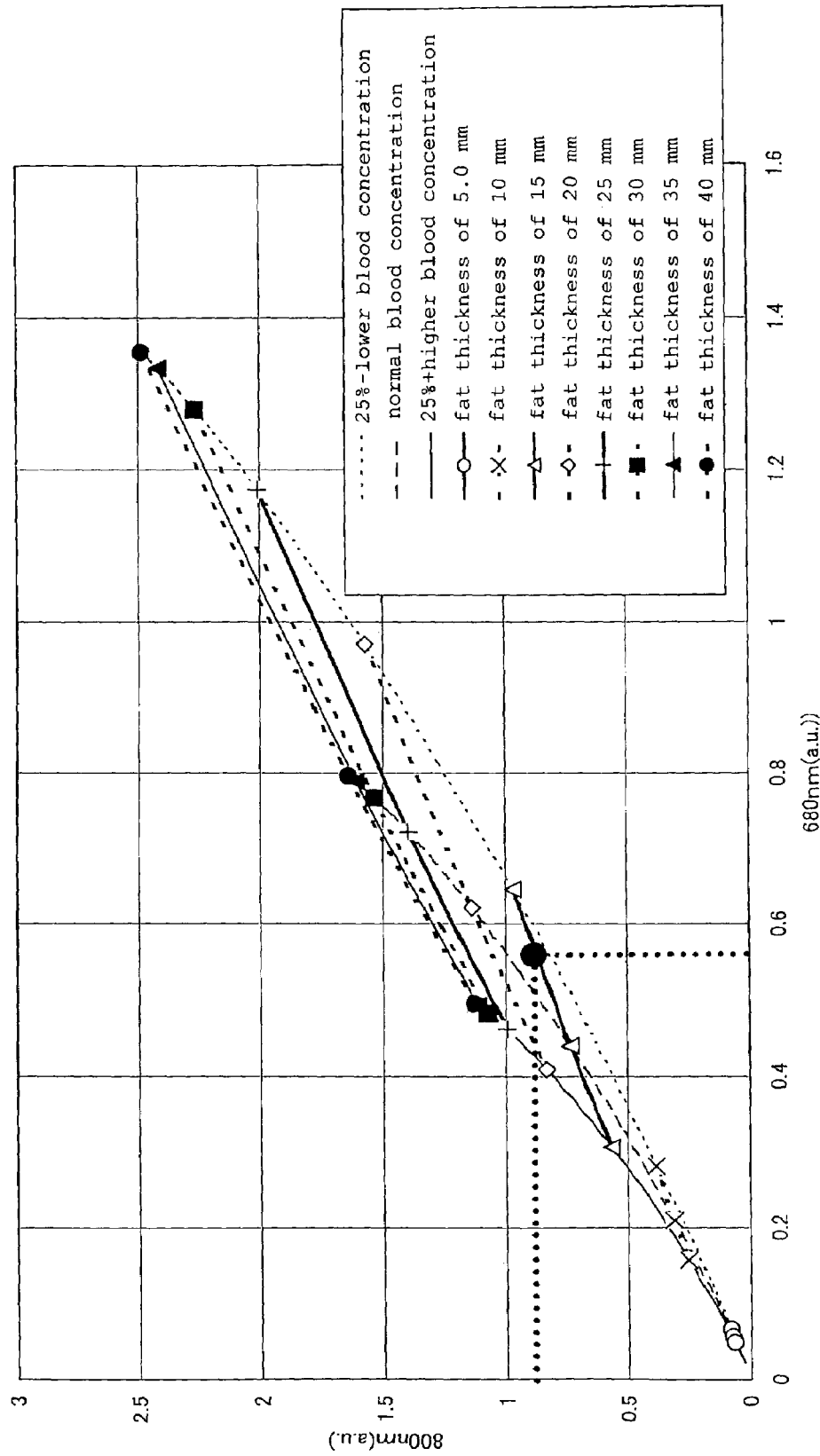
FIG. 11 is a graph showing relationships between the quantities of the 680-nm light and the 800-nm light for varied fat thicknesses and a constant blood concentration, which is calculated by simulation.
Figure 12:
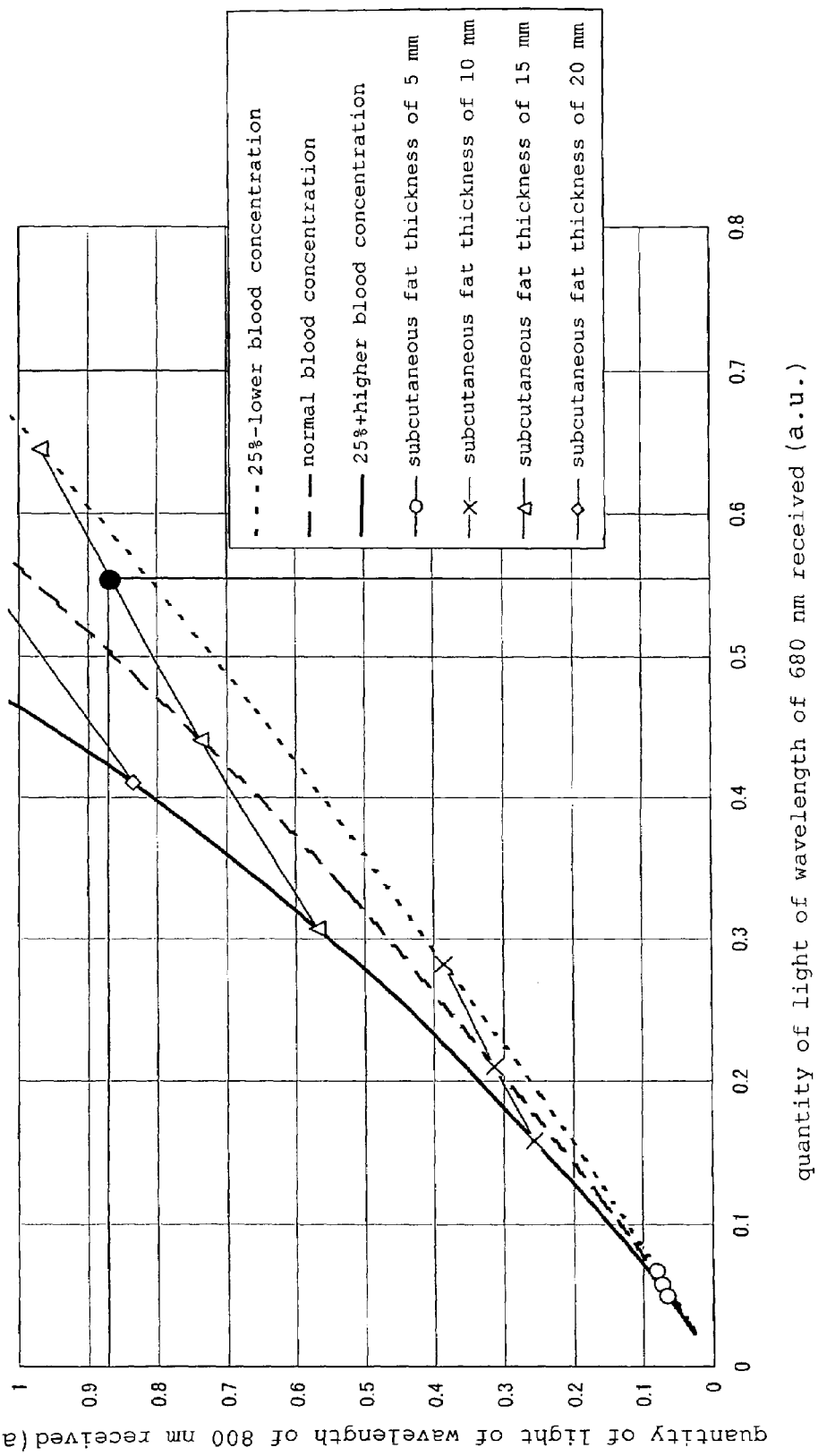
FIG. 12 is a graph obtained by enlarging the graph shown in FIG. 11 in the vicinity of the origin.
Figure 13:
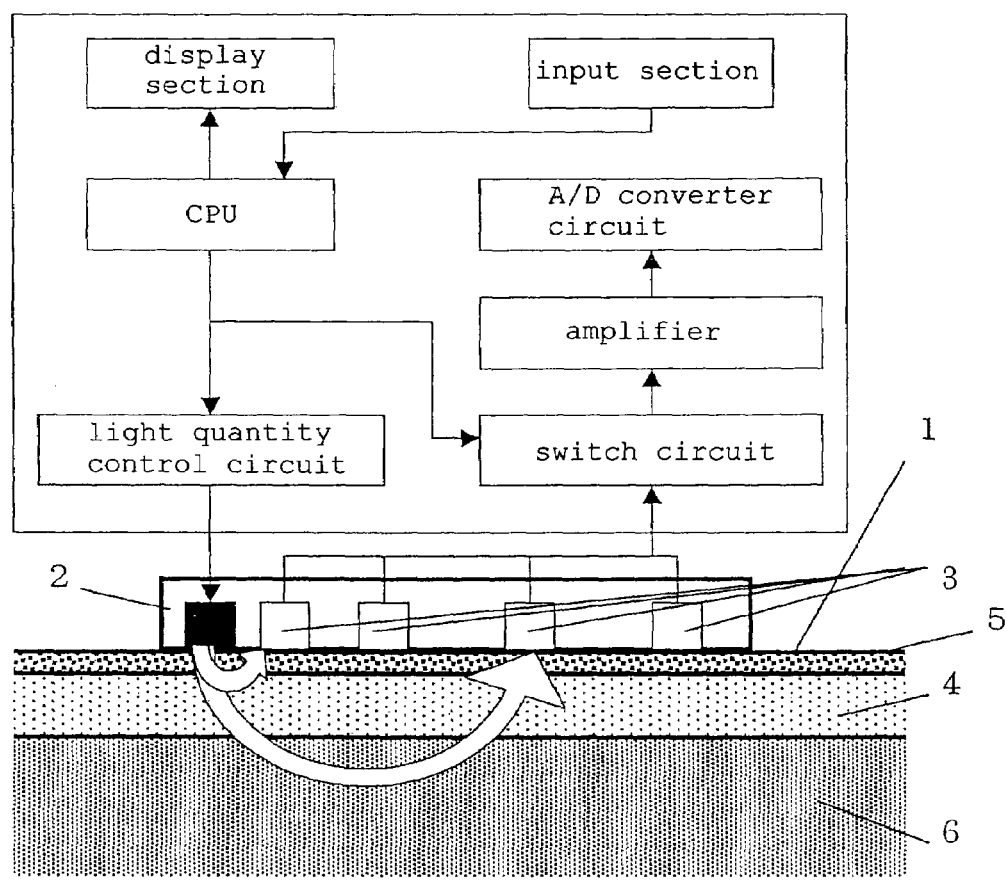
FIG. 13 is a diagram showing a conventional optical subcutaneous fat thickness measuring apparatus.

FIG. 11 shows overlaid plots representing a relationship between the quantities of light rays of wavelengths of 680 nm and 800 nm received for the case where the blood concentration in the fat is constant and the fat thickness varies and a relationship between the quantities of light rays of wavelengths of 680 nm and 800 nm received for the case where the fat thickness is constant and the blood concentration in the fat varies. That is, FIG. 11 shows the same plots as those shown in FIGS. 8 and 9 with the axes indicating the quantities of the light rays of the wavelengths received. And, FIG. 12 shows graphs obtained by enlarging the graphs shown in FIG. 11 for the range of the quantity of light received from 0 to 1. The FIGS. 11 and 12 corresponds to the relationship of the present invention, between subcutaneous fat thicknesses and quantities of plural light rays having different central wavelengths. It is preferable that the relationship such as shown in FIGS. 11 and 12 is stored in the calculator section 14 corresponding to the calculating means of the present invention.

As can be seen from FIG. 11, if the blood concentration in the fat remains constant and the subcutaneous fat thickness varies, the resulting graphs showing relationships between the quantities of the light rays of wavelengths of 680 nm and 800 nm received are parabolic. On the other hand, if the subcutaneous fat thickness remains constant and the blood concentration in the fat varies, the resulting graphs showing relationships between the quantities of the light rays of wavelengths of 680 nm and 800 nm received are linear.

In addition, FIG. 11 shows that as the subcutaneous fat gets thicker, the effect of the blood concentration on the blood concentration becomes larger, and the quantity of light received varies more significantly. For example, if the fat thickness is 5.0 mm and the blood concentration in the fat varies, the graph showing the relationship between the quantities of the light rays of wavelengths of 680 nm and 800 nm received appears in the vicinity of the origin in FIG. 11. In this case, as shown by the white circles, the quantity of light received is substantially the same for the cases where the blood concentration is normal, the blood concentration is 25% lower than the normal, and the blood concentration is 25% higher than the normal. To the contrary, if the fat thickness is 40 mm and the blood concentration in the fat varies, the graph showing the relationship between the quantities of the light rays of wavelengths of 680 nm and 800 nm received appears in the area farthest from the origin in FIG. 11. In this case, as shown by the black circles, the quantity of light received varies significantly for the cases where the blood concentration is 25% lower than the normal, the blood concentration is normal, and the blood concentration is 25% higher than the normal.

Here, drawing a line connecting the same marks, which represent the equal subcutaneous fat thickness, results in an approximate line.

The approximate lines for the subcutaneous fat thicknesses do not intersect with each other, as can be seen from FIGS. 11 and 12.

Therefore, if measurement is performed on a measuring object for which the subcutaneous fat thickness is not known using the 680-nm light and the 800-nm light, the measurement of the quantity of the 680-nm light received is plotted on the horizontal axis in FIG. 11 or 12, the measurement of the quantity of the 800-nm light received is plotted on the vertical axis in FIG. 11 or 12, and an approximate line is determined on which the intersection of the lines extending from the plots on the respective axes lies, the subcutaneous fat thickness defined by the approximate line can be regarded as the subcutaneous fat thickness of the relevant measuring object.

For example, if, for a measuring object for which the subcutaneous fat thickness is not know, the quantity of light received obtained in the measurement using the 800-nm light is 0.8, and the quantity of light received obtained in the measurement using the 680-nm light is 0.56, the intersection of the lines extending from those measurements plotted on the vertical and horizontal axes lies on an approximate line representing the fat thickness of 15 mm, as shown by the large black circles in FIGS. 11 and 12. This means that the subcutaneous fat thickness of the measuring object, which has been unknown, is 15 mm. Here, in the drawing, the large black circle is located between the triangle mark representing the normal blood concentration and the triangle mark representing the 25%-lower blood concentration. This means that the blood concentration in the subcutaneous fat of the measuring object falls between the normal blood concentration and the 25%-lower blood concentration. Here, a specific value of the blood concentration can be estimated based on the variations of the blood concentration and the quantity of light received shown in FIGS. 8 and 9, on which FIG. 12 is based.

As described above, according to this embodiment, if the quantity of light received is determined for the two light rays having central wavelengths of 800 nm and 680 nm, the subcutaneous fat thickness of the measuring object can be uniquely determined regardless of the blood concentration.

In this way, if adopting the relationship shown in FIGS. 11 and 12 as a previously predetermined relationship according to the present invention, the subcutaneous fat thickness can be correctly calculated from the quantities of two light rays of different wavelengths received, even if the blood concentration in the fat layer varies.

Now, a procedure of the measurement will be described.

According to the first embodiment, as described below, the compensating light receiving element 11 is not used.

Therefore, the subcutaneous fat thickness measuring apparatus according to the first embodiment may not include the compensating light receiving element 11. The compensating light receiving element 11 is used in a second embodiment.

As a first operation, in a state where the light source section 8 is off, the shaping section 7 is pressed against the surface of a living body 1.

As a second operation, the first light source 12 is turned on. Light 18 having reached the measuring light receiving element 10 is measured to obtain the quantity Y21 of measuring light received.

As a third operation, the first light source 12 is turned off, and the second light source 13 is turned on. The light 18 having reached the measuring light receiving element 10 is measured to obtain the quantity Y22 of measuring light received.

As a fourth operation, the thickness of the subcutaneous fat 14 is calculated in the calculator section 14. The thickness of the subcutaneous fat can be determined from FIGS. 11 and 12, which provide information about a relationship between the values Y22 and Y21 and the fat thickness.

Second Embodiment

In the following, a second embodiment of the present invention will be described.

The subcutaneous fat thickness measuring apparatus according to the second embodiment is configured the same as that according to the first embodiment, and thus, further description of the configuration will be omitted.

Here, an operation according to the second embodiment will be described primarily with reference to differences between the first embodiment and the second embodiment.

In the first embodiment, the subcutaneous fat thickness determined from the formula 1 and the quantities of light received, thereby suppressing the variation of the subcutaneous fat thickness, thereby compensating for the variation of light absorption by the subcutaneous fat.

Figure 6:
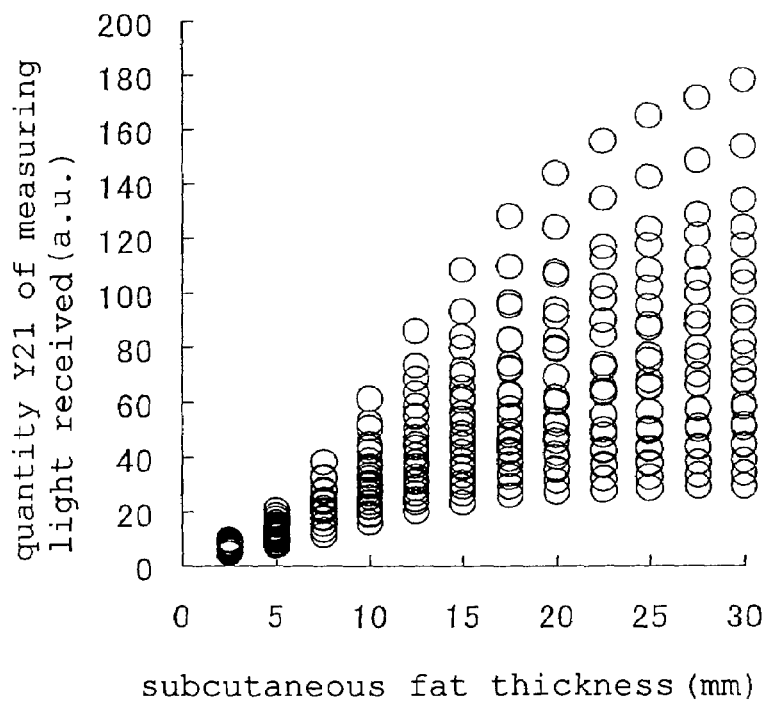
FIG. 6 is a graph showing a relationship between the quantity of measuring light received which, by simulation, takes into account variation of light absorption by skin and fat and the subcutaneous fat thickness.

However, the quantity of measuring light received has an error due to the effect of the variation of light scattering and light absorption by the skin 5. Here, if a simulation of making the light absorptions by the skin 5 and the subcutaneous fat 4 vary is performed, the quantity of received 800-nm light varies as shown by the white circles in FIG. 6, and it can be seen that it becomes more difficult to determine the fat thickness from the quantity of light received. To compensate for the effect of the variations of light absorption by the skin 5 and the subcutaneous fat 4 by simulation, the quantities Y11 and Y12 of compensating light measured by the compensating light receiving element 11 are also used. That is, according to the second embodiment, the quantities Y22 and Y21 of measuring light received and the quantities Y11 and Y12 of compensating light received are used to determine the subcutaneous fat thickness.

The subcutaneous fat thickness measuring apparatus according to the second embodiment compensates for the variation of the quantity of light received measured by the measuring light receiving element 10 due to a difference of the color of the skin by using the quantity of light received measured by the compensating light receiving element 11.

Now, a procedure of the measurement will be described.

As a first operation, in a state where the light source section 8 is off, the shaping section 7 is pressed against the surface of a living body 1.

As a second operation, the first light source 12 is turned on. Light 19 having reached the compensating light receiving element 9 is measured to obtain the quantity Y11 of compensating light received, and light 18 having reached the measuring light receiving element 10 is measured to obtain the quantity Y21 of measuring light received.

As a third operation, the first light source 12 is turned off, and the second light source 13 is turned on. Light 19 having reached the compensating light receiving element 11 is measured to obtain the quantity Y12 of compensating light received, and light 18 having reached the measuring light receiving element 10 is measured to obtain the quantity Y22 of measuring light received.

As a fourth operation, the thickness of the subcutaneous fat 4 is calculated in the calculator section 14. The thickness X of the subcutaneous fat 4 is represented by the following formula 2.

[Formula 2]

$$X = A \times Y22/Y12 + B \times Y21/Y11 + C \qquad \text{(formula 2)}$$

Here, characters A, B and C denote constants, which are determined by regression analysis from combinations of the quantities Y11, Y12, Y21 and Y22 of light received obtained by measurement for plural living bodies whose subcutaneous fat thicknesses X are known. The known subcutaneous fat thicknesses X can be determined from images taken by ultrasonic diagnostic equipment, MRI or X-ray CT.

Figure 7:
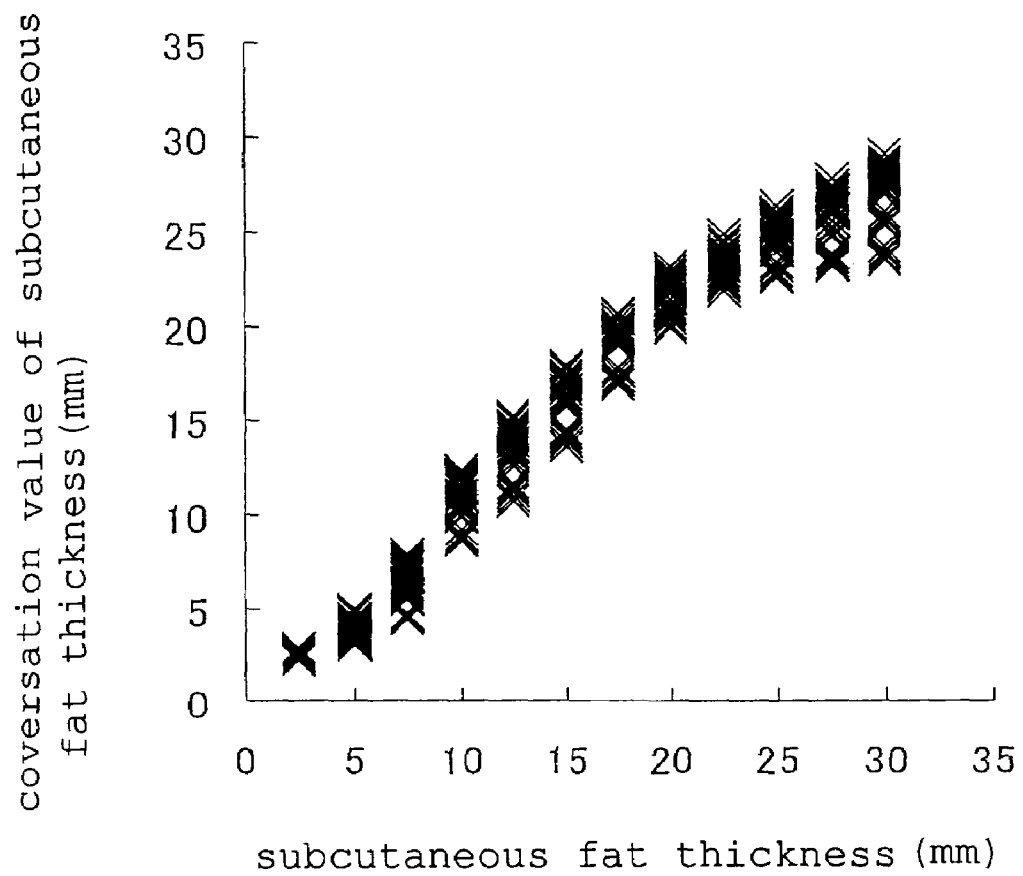
FIG. 7 is a graph showing a relationship between the conversation value of subcutaneous fat thickness value that is determined by a conversion formula and compensated for variations of light absorption by skin and fat and the subcutaneous fat thickness.

The quantities Y22, Y21, Y11 and Y12 of the two light rays of different wavelengths received for the case where the light absorptions by the skin 5 and the subcutaneous fat 4 vary are calculated, and the parameters A, B and C are determined based on the calculation result. FIG. 7 shows a relationship between estimated values of the subcutaneous fat thickness determined from the formula 2 and the quantities of light received and values of the subcutaneous fat thickness, which are simulation conditions. From comparison of FIGS. 6 and 7, it can be seen that the variation of the subcutaneous fat thickness is suppressed, and the variations of light absorption by the skin and the subcutaneous fat are compensated for.

While the description of this embodiment has been focused on the determination of the subcutaneous fat thickness, the application of the present invention is not limited to the subcutaneous fat thickness. Information other than the subcutaneous fat thickness, such as the body fat percentage, can also be obtained. In such a case, the body fat percentage can be calculated from the subcutaneous fat thickness and information about all or some of weight, height, sex, age, measurement part and the like.

Furthermore, while two light rays of different wavelengths, specifically, light having a central wavelength of 680 nm and light having a central wavelength of 800 nm, have been used in the embodiments described above, three or more kinds of central wavelength light rays may be used in some cases.

A program according to the present invention is a program that makes a computer execute all or some of the steps of the subcutaneous fat thickness measuring method according to the present invention described above and may be a program that runs in cooperation with the computer.

In addition, according to the present invention, there is provided a medium that stores the program that makes a computer execute all or some of the operations in all or some of the steps of the subcutaneous fat thickness measuring apparatus according to the present invention described above, the medium according to the present invention may be a medium that can be read by a computer so that the program read can execute the operations described above in cooperation with the computer.

The expression "some of the steps" means some steps of the plural steps or some operations in a certain step.

In addition, the present invention includes a computer-readable recording medium in which the program according to the present invention is recorded.

As an implementation, the program according to the present invention may be recorded in a computer-readable recording medium and run in cooperation with a computer.

As an implementation, the program according to the present invention may be transmitted via a communication medium and read by a computer and run in cooperation with the computer.

A data structure according to the present invention may be a database, a data format, a data table, a data list or a data type.

Furthermore, the recording medium may be a ROM or the like, and the communication medium may be a communication mechanism, such as the Internet, or light, radio wave, acoustic wave or the like.

The computer according to the present invention described above is not exclusively hardware, such as a CPU, but may be firmware or OS or may include peripheral equipment.

In addition, as described above, the arrangement according to the present invention may be implemented in the form of software or hardware.

With the subcutaneous fat measuring method, the subcutaneous fat measuring apparatus, the program and the recording medium according to the present invention, subcutaneous fat information, such as subcutaneous fat thickness, can be obtained with high precision and high reproducibility, and the subcutaneous fat measuring method, the subcutaneous fat measuring apparatus, the program and the recording medium according to the present invention can be advantageously applied to optical measurement of the thickness of local subcutaneous fat.

What is claimed is:

1. A subcutaneous fat thickness measuring method, comprising:

irradiating a surface of a living body with a first light ray having a first central wavelength falling between 650 nm and 700 nm and a second light ray having a second central wavelength falling between 800 nm and 850 nm, the first and second light rays being irradiated into a same subcutaneous fat layer of the living body and having different absorption levels in blood;

receiving, at one site on the surface of the living body, the first and second light rays that have traveled a path through the same subcutaneous fat layer and emerged from the surface of the living body, and measuring the quantity of each of the first light ray and the second light ray received; and calculating the thickness of subcutaneous fat of the living body from the quantities of the first light ray and the second light ray received and measured by using plural relationships between a known subcutaneous fat thickness and quantities of the first and second light rays obtained for different blood concentrations in the known subcutaneous fat thickness, and using as parameters the quantities of the first and second light rays for compensating for measurement errors due to variation of the blood concentration in the subcutaneous fat.

2. The subcutaneous fat thickness measuring method according to claim 1, wherein another light ray for compensating for the variation of the quantities of the first and second light rays due to a difference of the color of skin is received at a site, which is different from the site where the first and second light rays are received, on the surface of the living body.

3. The subcutaneous fat thickness measuring method according to claim 2, wherein said another light ray includes a third light ray and a fourth light ray, the third light ray having the same wavelength as that of the first light ray, and the fourth light ray having the same wavelength as that of the second light ray, wherein the thickness (X) of subcutaneous fat of the living body is calculated by use of the following formula based on the quantities (Y21, Y22, Y11 and Y12) of the first, second, third and fourth light ray received and measured:

$X=A*Y22/Y12+B*Y21/Y11+C$ where character A, B and C denote constants, which are determined by regression analysis from combinations of the quantities Y21, Y22, Y11 and Y12 of light received obtained by measurement for plural living bodies whose subcutaneous fat thickness X are known in case that blood concentrations in the subcutaneous fat are different each other.

4. The subcutaneous fat thickness measuring method according to claim 1, further comprising:

calculating the body fat percentage of a measuring object person from the calculated thickness of the subcutaneous fat by using information about all or some of the weight, the sex, the height, the age and the measurement part of the measuring object person having the surface of the living body.

5. A subcutaneous fat thickness measuring apparatus, comprising:

an irradiation device for irradiating a surface of a living body with a first light ray having a first central wavelength falling between 650 nm and 700 nm and a second light ray having a second central wavelength falling between 800 nm and 850 nm, the first and second light rays being irradiated into a same subcutaneous fat layer of the living body and having different absorption levels in blood;

a light receiving device for receiving, at one site on the surface of the living body, the first and second light rays that have traveled a path through the same subcutaneous fat layer and emerged from the surface of the living body, and measuring the quantity of each of the first light ray and the second light ray received; and a calculation device for calculating the thickness of subcutaneous fat of the living body from the quantities of the first light ray and the second light ray received and measured by using plural relationships between a known subcutaneous fat thickness and quantities of the first and second light rays obtained for different blood concentrations in the known subcutaneous fat thickness, wherein the calculation device includes using as parameters the quantities of the first and second light rays for compensating for measurement errors due to variation of the blood concentration in the subcutaneous fat.

6. The subcutaneous fat thickness measuring apparatus according to claim 5, wherein the light receiving device receives another light ray for compensating for the variation of the quantities of the first and second light rays due to a difference of the color of skin at a site, which is different from the site where the first and second light rays are received, on the surface of the living body.

7. The subcutaneous fat thickness measuring apparatus according to claim 6, wherein said another light ray includes a third light ray and a fourth light ray, the third light ray having the same wavelength as that of the first light ray, and the fourth light ray having the same wavelength as that of the second light ray, wherein the calculation device calculates the thickness (X) of subcutaneous fat of the living body by use of the following formula from the quantities (Y21, Y22, Y11 and Y12) of the first, second, third and fourth light ray received and measured by the light receiving device:

$X=A*Y22/Y12+B*Y21/Y11+C$ where character A, B and C denote constants, which are determined by regression analysis from combinations of the quantities Y21, Y22, Y11 and Y12 of light received obtained by measurement for plural living bodies whose subcutaneous fat thickness X are known in case that blood concentrations in the subcutaneous fat are different each other.

8. The subcutaneous fat thickness measuring apparatus according to claim 5, further comprising:

a body fat percentage calculation device for calculating the body fat percentage of a measuring object person from the calculated thickness of the subcutaneous fat by using information about all or some of the weight, the sex, the height, the age and the measurement part of the measuring object person having the surface of the living body.

9. A subcutaneous fat thickness measuring method, comprising:

irradiating a surface of a living body with a first light ray having a first central wavelength falling between 650 nm and 700 nm and a second light ray having a second central wavelength falling between 800 nm and 850 nm, the first and second light rays having different absorption levels in blood;

receiving, at one site on the surface of the living body, the first and second light rays that have traveled a path through a same subcutaneous fat layer and emerged from the surface of the living body, and measuring the quantity of each of the first light ray and the second light ray received; and calculating the thickness of subcutaneous fat of the living body from the quantities of the first light ray and the second light ray received and measured by using plural relationships between a known subcutaneous fat thickness and quantities of the first and second light rays obtained for different blood concentrations in the known subcutaneous fat thickness, and using a conversion formula determined by regression analysis using as parameters the quantities of the first and second light rays for compensating for measurement errors due to variation of the blood concentration in the subcutaneous fat.

10. A subcutaneous fat thickness measuring apparatus, comprising:

an irradiation device for irradiating a surface of a living body with a first light ray having a first central wavelength falling between 650 nm and 700 nm and a second light ray having a second central wavelength falling between 800 nm and 850 nm, the first and second light rays having different absorption levels in blood;

a light receiving device for receiving, at one site on the surface of the living body, the first and second light rays that have traveled a path through a same subcutaneous fat layer and emerged from the surface of the living body, and measuring the quantity of each of the first light ray and the second light ray received; and a calculation device for calculating the thickness of subcutaneous fat of the living body from the quantities of the first light ray and the second light ray received and measured by using plural relationships between a known subcutaneous fat thickness and quantities of the first and the second light rays obtained for different blood concentrations in the known subcutaneous fat thickness;

wherein the calculation device includes using a conversion formula determined by regression analysis using as parameters the quantities of the first and second light rays for compensating for measurement errors due to variation of the blood concentration in the subcutaneous fat.

11. A subcutaneous fat thickness measuring method, comprising:

irradiating a surface of a living body with a first light ray having a first central wavelength falling between 650 nm and 700 nm and a second light ray having a second central wavelength falling between 800 nm and 850 nm, the first and second light rays being irradiated into a same subcutaneous fat layer of the living body and having different absorption levels in blood;

receiving, at one site on the surface of the living body, the first and second light rays that have traveled a path through the same subcutaneous fat layer and emerged from the surface of the living body, and measuring the quantity of each of the first light ray and the second light ray received; and calculating the thickness of subcutaneous fat of the living body from the quantities of the first light ray and the second light ray received and measured by using a relationship between a known subcutaneous fat thickness and quantities of the first and second light rays obtained from the known subcutaneous fat thickness.

12. The subcutaneous fat thickness measuring method according to claim 11, wherein the thickness (X) of subcutaneous fat of the living body is calculated by use of the following formula based on the quantities (Y21 and Y22) of the first and second light ray received and measured:

$$X = A*Y22 + B*Y21 + C$$

where character A, B and C denote constants, which are determined by regression analysis from combinations of the quantities Y21 and Y22 of light received obtained by measurement for plural living bodies whose subcutaneous fat thickness X are known in case that blood concentrations in the subcutaneous fat are different each other.

13. A subcutaneous fat thickness measuring apparatus, comprising:

an irradiation device for irradiating a surface of a living body with a first light ray having a first central wavelength falling between 650 nm and 700 nm and a second light ray having a second central wavelength falling between 800 nm and 850 nm, the first and second light rays being irradiated into a same subcutaneous fat layer of the living body and having different absorption levels in blood;

a light receiving device for receiving, at one site on the surface of the living body, the first and second light rays that have traveled a path through the same subcutaneous fat layer and emerged from the surface of the living body, and measuring the quantity of each of the first light ray and the second light ray received; and a calculation device for calculating the thickness of subcutaneous fat of the living body from the quantities of the first light ray and the second light ray received and measured by using a relationship between a known subcutaneous fat thickness and quantities of the first and the second light rays obtained from the known subcutaneous fat thickness.

14. The subcutaneous fat thickness measuring apparatus according to claim 13, wherein the relationship used by said calculation device for calculating the thickness of the subcutaneous fat is determined by simulation.

15. The subcutaneous fat thickness measuring apparatus according to claim 13, wherein the calculation device calculates the thickness (X) of subcutaneous fat of the living body by use of the following formula from the quantities (Y21 and Y22) of the first and second light ray received and measured:

$$X = A*Y22 + B*Y21 + C$$

where character A, B and C denote constants, which are determined by regression analysis from combinations of the quantities Y21 and Y22 of light received obtained by measurement for plural living bodies whose subcutaneous fat thickness X are known in case that blood concentrations in the subcutaneous fat are different each other.

16. A subcutaneous fat thickness measuring method, comprising:

irradiating a surface of a living body with a first light ray having a first central wavelength falling between 650 nm and 700 nm and a second light ray having a second central wavelength falling between 800 nm and 850 nm, the first and second light rays being irradiated into a same subcutaneous fat layer of the living body;

receiving, at one site on the surface of the living body, the first and second light rays that have traveled a path through the same subcutaneous fat layer and emerged from the surface of the living body, and measuring the quantity of each of the first light ray and the second light ray received; and calculating the thickness of subcutaneous fat of the living body based on an equation that expresses a relationship between a) the quantity of each of the first light ray and the second light ray received; and b) the thickness of the same subcutaneous fat layer;

wherein the equation is generated from measuring quantities of the first light ray and the second light ray traveling through subcutaneous fat layers of known thickness.

17. A subcutaneous fat thickness method according to claim 16, wherein the equation is generated using regression analysis of the quantities of the first light ray and the second light traveling through subcutaneous fat layers and the known thicknesses.

* * * * *

UNITED STATES PATENT AND TRADEMARK OFFICE
CERTIFICATE OF CORRECTION

PATENT NO. : 7,720,527 B2  Page 1 of 1
APPLICATION NO. : 10/986719
DATED : May 18, 2010
INVENTOR(S) : Kondoh et al.

It is certified that error appears in the above-identified patent and that said Letters Patent is hereby corrected as shown below:

On the Cover Page, at Item (73), Assignee:

"Panasonic Corp., Osaka (JP)" should read --Panasonic Electric Works Co., Ltd., Osaka (JP).--

Signed and Sealed this

Seventeenth Day of August, 2010

David J. Kappos
*Director of the United States Patent and Trademark Office*